United States Patent
Puthiaparampil et al.

(10) Patent No.: US 7,232,920 B2
(45) Date of Patent: Jun. 19, 2007

(54) PROCESS FOR STEREOSELECTIVE REDUCTION OF β-KETOESTERS

(75) Inventors: Tom Thomas Puthiaparampil, Karnataka (IN); Acharya Poornaprajna, Karnataka (IN); Chandrashekar Aswathanarayanappa, Karnataka (IN); Madhavan Sridharan, Karnataka (IN); Sambasivam Ganesh, Karnataka (IN)

(73) Assignee: Biocon, Bangalore (IN)

( * ) Notice: Subject to any disclaimer, the term of this patent is extended or adjusted under 35 U.S.C. 154(b) by 108 days.

(21) Appl. No.: 10/483,479

(22) PCT Filed: Apr. 22, 2003

(86) PCT No.: PCT/IN03/00166

§ 371 (c)(1),
(2), (4) Date: Aug. 12, 2004

(87) PCT Pub. No.: WO2004/094343

PCT Pub. Date: Nov. 4, 2004

(65) Prior Publication Data

US 2004/0259946 A1    Dec. 23, 2004

(51) Int. Cl.
C07C 69/76    (2006.01)
C07C 255/21   (2006.01)
C07F 7/18     (2006.01)

(52) U.S. Cl. .................. 556/437; 558/441; 560/57
(58) Field of Classification Search ............... None
See application file for complete search history.

(56) References Cited

U.S. PATENT DOCUMENTS

| | | | |
|---|---|---|---|
| 4,645,854 A | 2/1987 | Verhoeven et al. | |
| 6,274,740 B1 | 8/2001 | Lin et al. | |
| 6,433,213 B1* | 8/2002 | Bosch et al. | 558/441 |
| 6,528,661 B2 | 3/2003 | Niddam et al. | |
| 2002/0099224 A1 | 7/2002 | Niddam et al. | |
| 2003/0114685 A1 | 6/2003 | Niddam-Hildesheim et al. | |
| 2003/0175338 A1 | 9/2003 | Singh et al. | |

FOREIGN PATENT DOCUMENTS

| | | | |
|---|---|---|---|
| EP | 0424929 A1 | | 5/1991 |
| WO | WO 97/03960 | | 2/1997 |
| WO | WO 98/04543 | * | 2/1998 |
| WO | WO 02/43667 A2 | | 6/2002 |
| WO | WO 03/004450 A1 | | 1/2003 |
| WO | WO 03/004455 A2 | | 1/2003 |
| WO | WO03/004456 A1 | | 1/2003 |
| WO | WO 03/016317 A1 | | 2/2003 |

OTHER PUBLICATIONS

Jacks et al., STN International, HCAPLUS Database, Columbus, OH, Accession No. 1998:102860, Reg. No. 125971-93-9 (2006)).*

International Search Report for corresponding PCT application PCT/IN03/00166.

Hamada et al., "New Methods and Reagents in Organic Synthesis. A Practical Method for the Preparation of Optically Active N-Protected α-Amino Aldehydes and Peptide Aldehydes," *Chem Pharm Bull*, 30(5): 1921-1924, 1982.

Luche, "Lanthanides in Organic Chemistry. 1. Selective 1,2 Reductions of Conjugated Ketones," *JACS*, 100(7): 2226-2227, 1978.

Boutin, et al., "α-Amino Acid Derivatives as Chiral Educts for Asymmetric Products. Synthesis of Sphinogosine from α'-Amino-α,β-ynones," *J. Org. Chem.*, 51(26): 5320-5327, 1986.

Rucker, et al., "Stereoselective Reduction of Cyclic 2,3-Epoxyketones to Trans-2,3-Epoxyalcohols," *Synth. Comm.*, 10(8): 623-626, 1980.

Bonadies, et al., "Studies on Asymmetric Synthesis of β-Hydroxy-δ-Lactone Inhibitors of HMGCoA Reductase. A New Preparation of the Lactone Moiety of Compactin," *Tet Letts*, 28(6): 703-706, 1987.

Oehrlein R et al., "Chemoenzymatic approach to statin side-chain building blocks" Advanced Synthesis Catalysis (2003), 345 (6+7), 713-715.

(Continued)

*Primary Examiner*—Kamal A. Saeed
*Assistant Examiner*—Andrew B. Freistein
(74) *Attorney, Agent, or Firm*—Andrea L. C. Robidoux; Choate, Hall & Stewart LLP

(57) ABSTRACT

In one aspect, the invention provides a process for the preparation of compounds of Formula I

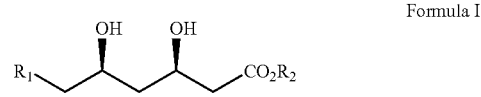

Formula I wherein $R_1$ is —CN, —OP, alkyl, aryl or heteroaryl; wherein P represents any suitable protecting group; and $R_2$ is alkyl or aryl;
by reacting a compound of Formula II

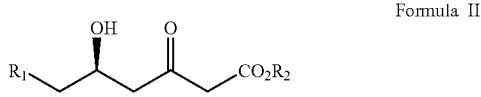

Formula II wherein $R_1$ is —CN, —OP, alkyl, aryl or heteroaryl; wherein P represents any suitable protecting group; and $R_2$ is alkyl or aryl;
with
a reducing agent (e.g. sodium borohydride) in the presence of a metal halid (e.g. $CeCl_3$) or a metal alkoxid (e.g. $Ti(OiPr)_4$).

4 Claims, No Drawings

OTHER PUBLICATIONS

Woo et al., "Atorvastatin, an HMG-CoA reductase inhibitor and effective lipid-regulating agent. Part III. Syntheses of [2H5]-, [13C8], and [13C7, 15N] atorvastatin and their application in metabolic and pharmacokinetic studies", Journal of Labeled Compounds Radiopharmaceuticals (1999), 42(2), 135-145.

Lee et al., "Atorvastatin, an HMG-CoA reductase inhibitor and effective lipid-regulating agent. Part II. Synthesis of side chain-labeled [14C] atorvastatin", Journal of Labeled Compounds Radiopharmaceuticals (1999), 42(2), 129-133.

Woo et al., "Atorvastatin, an HMG-CoA reductase inhibitor and effective lipid-regulating agent. Part I. Synthesis of ring-labeled [14C] atorvastatin", Journal of Labeled Compounds Radiopharmaceuticals (1999), 42(2), 121-127.

Radl et al., "An improved synthesis of 1,1-dimethylethyl-6-cyanomethyl-2,2-dimethyl-1,3-dioxane-4-acetate, a key intermediate for atorvastatin synthesis", Tetrahedron Letters (2002), 43(11), 2087-2090.

Manzoni et al., "Biosynthesis and biotechnological production of statins by filamentous fungi and application of these cholesterol-lowering drugs", Applied Microbiology and Biotechnology (2002), 58(5), 555-564.

Roth, Bruce D., "The discovery and development of atorvastatin, a potent novel hypolipidemic agent", Progress in Medicinal Chemistry (2002), 40, 1-22.

Wierzbicki, Anthony S., "Atorvastatin", Expert Opinion on Pharmacotherapy (2001), 2(5), 819-830.

Graul et al., "Atorvastatin calcium", Drugs of the future (1997), 22(9), 956-968.

Baumann et al., "The convergent synthesis of CI-981, an optically active, highly potent, tissue-selective inhibitor of HMG-CoA reductase", Tetrahedron Letters (1992), 33(17), 2283-2284.

* cited by examiner

PROCESS FOR STEREOSELECTIVE REDUCTION OF β-KETOESTERS

PRIORITY CLAIM

The present application claims the benefit under 35 U.S.C. § 371 of International Application No.: PCT/IN03/00166, filed Apr. 22, 2003, the entire contents of each of these applications are hereby incorporated by reference.

FIELD OF THE INVENTION

The present invention relates to a novel stereoselective process for preparing optically active dihydroxy ester derivatives of Formula I which are useful intermediates for the synthesis of HMG-CoA enzyme inhibitors like atorvastatin, cerivastatin, rosuvastatin, itavastatin, and fluvastatin.

BACKGROUND OF THE INVENTION

Ester derivatives of the Formula I

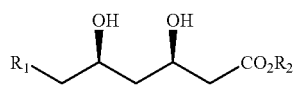

Formula I wherein $R_1$ is —CN, —OP, alkyl, aryl or heteroaryl; wherein P represents any suitable protecting group; and $R_2$ is alkyl or aryl;

are valuable chiral synthons for synthesizing compounds which are known anti-hyptercholesterolemic agents having an inhibitory effect on HMG-CoA reductase (See U.S. Pat. Nos. 5,003,080, 5,169,857, 5,354,772; PCT Application WO 01 85702; European Patent Application EP 0304063).

The most common approach for achieving stereoselective synthesis of compounds of Formula I is the reduction of Formula II

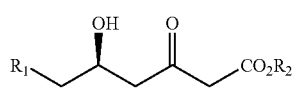

Formula II wherein $R_1$ is —CN, —OP, alkyl, aryl or heteroaryl; wherein P represents any suitable protecting group; and $R_2$ is alkyl or aryl;

using special borane reagents (See U.S. Pat. Nos. 5,273,995, 5,470,981, 5,489,691). However, reagents such as methoxydiethylborane are hazardous and expensive.

U.S. Pat. No. 6,001,615 describes an enzymatic synthetic route. This process, however, is not industrially scalable and involves large volumes.

U.S. Pat. No. 5,399,722 describes a process starting from commercially available ethyl-ω-chloroacetoacetate or its benzyloxy derivative. Disadvantages of this process are that a stereoselective reduction using a ruthenium-BINAP catalyst is employed and the desired compound of Formula I is obtained in six steps.

U.S. Pat. No. 5,481,009 describes a process starting from 4-phenyl-3-butenoic acid and achieves the desired compound in about 5 steps. The process uses hazardous steps (e.g. ozonolysis) to obtain the desired product.

Exemplary synthetic approaches for the preparation of statins using compounds of Formula I are depicted in Schemes 1-6.

The present invention has several advantages over known methods. The process of the present invention is safe and non-hazardous, cost-effective, industrially scalable, requires few steps, and is commercially viable.

SUMMARY OF THE INVENTION

In one aspect, the present invention provides a novel process for the preparation of compounds of Formula I

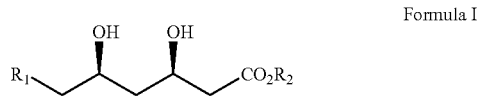

Formula I wherein $R_1$ is —CN, —OP, alkyl, aryl or heteroaryl; wherein P represents any suitable protecting group; and $R_2$ is alkyl or aryl;

the process comprising a step of reacting a compound of Formula II

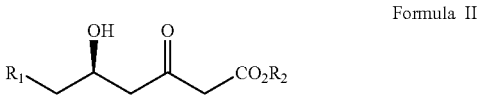

Formula II wherein $R_1$ is —CN, —OP, alkyl, aryl or heteroaryl; wherein P represents any suitable protecting group; and $R_2$ is alkyl or aryl;

with sodium borohydride in presence of a metal halide (e.g. $CeCl_3$) or metal alkoxide (e.g. $Ti(OiPr)_4$) (See Scheme I). In one embodiment, the reagents are non-hazardous, easily available and inexpensive.

DETAILED DESCRIPTION OF CERTAIN PREFERRED EMBODIMENTS OF THE INVENTION

The compound of Formula II is an important intermediate for the preparation of many drug molecules, especially HMG Co-A reductase inhibitors. HMG Co-A reductase inhibitors are useful as inhibitors of the enzyme 3-hydroxy-3-methylglutaryl-coenzyme A reductase (HMG CoA reductase) and are thus useful as hypolipidemic or hypocholesterolemic agents.

In one aspect, the process of the present invention is a new, improved, industrially scalable, economical, and commercially feasible method for preparing intermediates used for the preparation of HMG CoA reductase inhibitors. An exemplary process according to the present invention is depicted in Scheme 1.

Scheme 1:
Preparation of compounds of Formula I

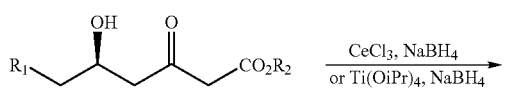

Formula II

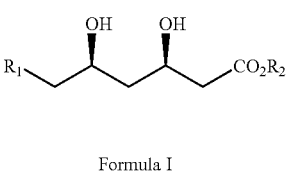

Formula I wherein $R_1$ is —CN, —OP, alkyl, aryl or heteroaryl; wherein P represents any suitable protecting group; and $R_2$ is alkyl or aryl;

In certain embodiments, the present invention provides a novel process for the preparation of compounds of Formula I

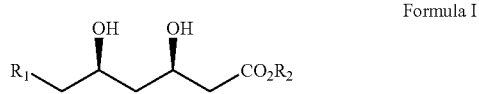

Formula I wherein $R_1$ is —CN, —OP, alkyl, aryl or heteroaryl; wherein P represents any suitable protecting group; and $R_2$ is alkyl or aryl;

by reacting a compound of Formula II

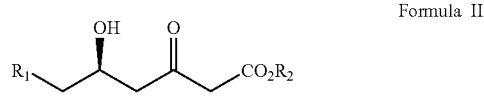

Formula II wherein $R_1$ is —CN, —OP, alkyl, aryl or heteroaryl; wherein P represents any suitable protecting group; and $R_2$ is alkyl or aryl; with sodium borohydride in the presence of a metal halide or a metal alkoxide. In one embodiment, the metal halide is anhydrous $CeCl_3$. In another embodiment, the metal halide is hydrated $CeCl_3$. In yet another embodiment, the metal alkoxide is $Ti(OiPr)_4$.

The reagents are easily available and inexpensive.

Compounds of Formula I are important intermediates for the preparation of HMG Co-A reductase inhibitors. Exemplary synthetic approaches for the preparation of such inhibitors using compounds of Formula I can be found in schemes 2-6. (See scheme 2 (Atorvastatin), scheme 3 (Cerivastatin), scheme 4 (Itavastatin), scheme 5 (Rosuvastatin) and scheme 6 (Fluvastatin)).

Scheme 2:
Synthesis of Atorvastatin Calcium from Formula I

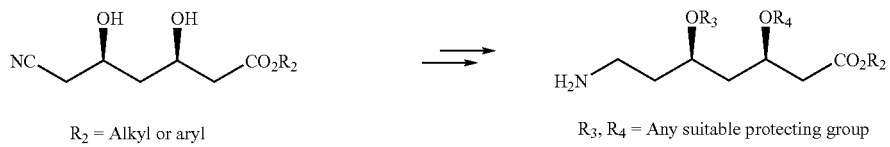

$R_2$ = Alkyl or aryl $R_3, R_4$ = Any suitable protecting group

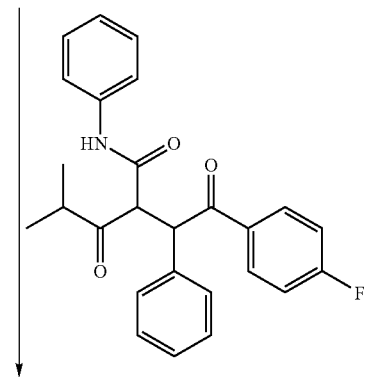

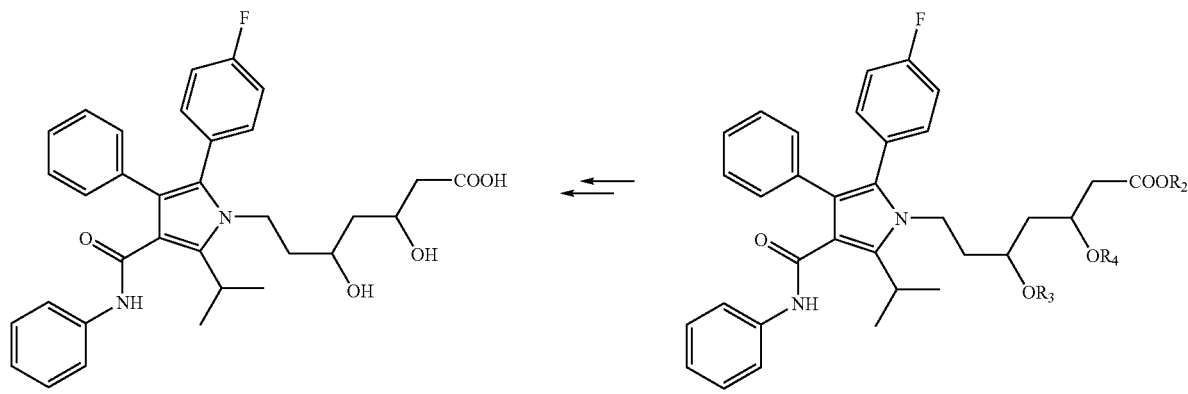
-continued
Scheme 3:
Synthesis of Cerivastatin
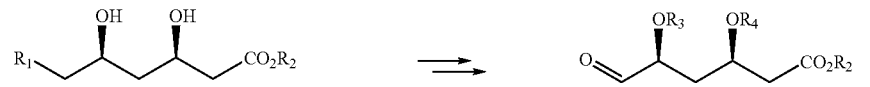
$R_1$ = OP (P = any suitable protecting group)
$R_2$ = Alkyl or aryl
$R_3$, $R_4$ = Any suitable protecting group
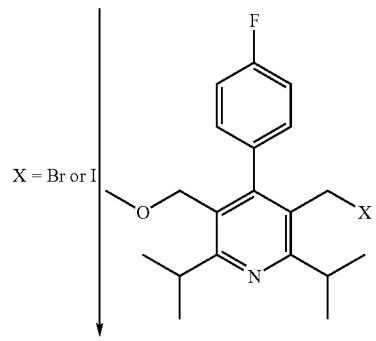
X = Br or I
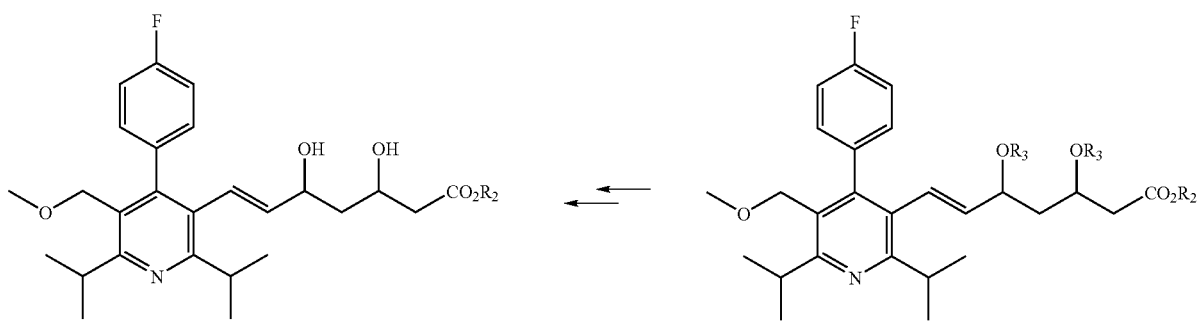

Scheme 4:
Synthesis of Itavastatin
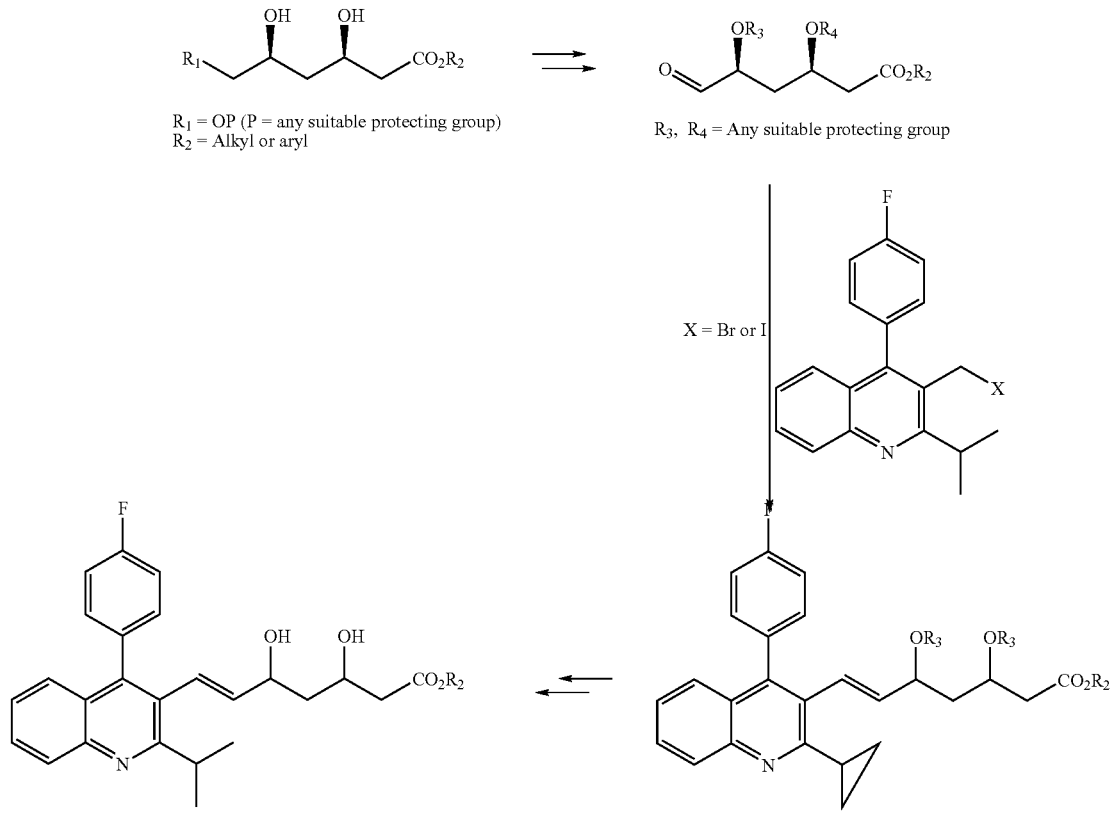
Scheme 5:
Synthesis of Rosuvastatin
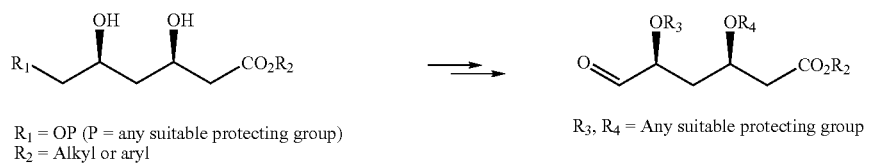
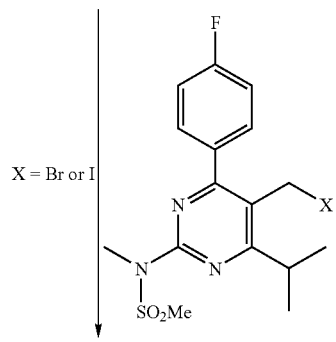

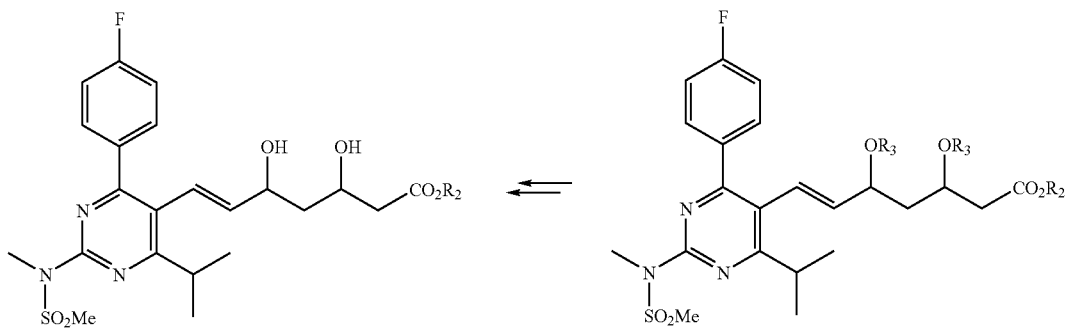
Scheme 6:
Synthesis of Fluvastatin
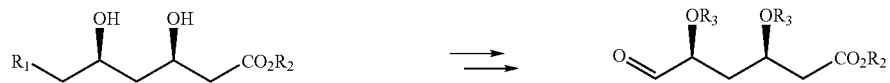
$R_1$ = OP (P = any suitable protecting group)
$R_2$ = Alkyl or aryl
$R_3$, $R_4$ = Any suitable protecting group
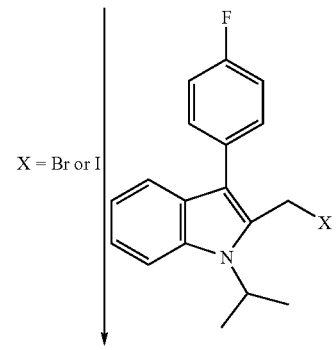
X = Br or I
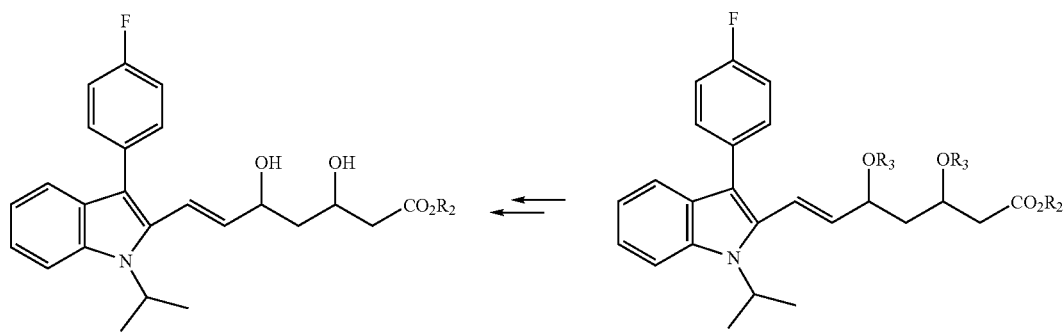

The illustrated embodiments have been set forth only for the purposes of example and should not be taken as limiting the invention. Therefore, it should be understood that, within the scope of the appended claims, the invention may be practiced other than specifically described herein.

EXAMPLE 1

Preparation of tert-butyl (3R,5R)-6-cyano-3,5-dihydroxyhexanoate

A solution of tert-butyl (5R)-6-cyano-5-hydroxy-3-oxo-hexanoate (10 g, 0.044 mol) in THF (60 mL) was stirred under nitrogen and methanol (20 mL) was added. The reaction mixture was stirred for 15 min. and cooled to −50° C. to −55° C. Anhydrous $CeCl_3$ (10.8 g, 0.044 mol) was added and stirred for 30 min., maintaining the temperature between −50 and −55° C. Sodium borohydride (2.5 g, 0.066 mol) was added in 6 portions maintaining the temperature between −70 and −90° C. The resulting mixture was stirred for 1 h at the same temperature. After warming the reaction mixture to room temperature (RT), it was concentrated to a residue under vacuum at about 45° C. Methanol (60 mL) was added and the resulting mixture was concentrated. The resulting residue was cooled to RT, water (50 mL) was added and the resulting aqueous mixture was extracted with ethyl acetate (100 mL×2). The combined organic layer was washed with brine solution (50 mL), and concentrated to obtain the title compound. Yield: 9 g.

EXAMPLE 2

Preparation of tert-butyl (3R,5R)-6-cyano-3,5-dihydroxyhexanoate

A solution of tert-butyl (5R)-6-cyano-5-hydroxy-3-oxo-hexanoate (10 g, 0.044 mol) in THF (60 mL) was stirred under nitrogen and methanol (20 mL) was added. The reaction mixture was stirred for 15 min. and cooled to −50° C. to −55° C. $CeCl_3.7H_2O$ (16.4 g, 0.044 mol) was added and stirred for 30 min., maintaining the temperature between −50 and −55° C. Sodium borohydride (2.5 g, 0.066 mol) was added in 6 portions maintaining the temperature between −70 and −90° C. The resulting mixture was stirred for 1 h at the same temperature. After warming the reaction mixture to RT, it was concentrated to a residue under vacuum at about 45° C. Methanol (60 mL) and the resulting mixture was concentrated. The resulting residue was cooled to RT, water (50 mL) was added and the resulting aqueous mixture was extracted with ethyl acetate (100 mL×2). The combined organic layer was washed with brine solution (50 mL), and concentrated to obtain title compound. Yield: 5 g.

EXAMPLE 3

Preparation of tert-butyl (3R,5R)-6-cyano-3,5-dihydroxyhexanoate

A solution of tert-butyl (5R)-6-cyano-5-hydroxy-3-oxo-hexanoate (10 g, 0.044 mol) in THF (60 mL) was stirred under nitrogen and methanol (20 mL) was added. The reaction mixture was stirred for 15 min. Ti(IV)isopropoxide (12.5 g, 0.044 mol) was added and stirred for 30 min. at room temperature. After cooling the reaction mixture to −50° C. to −55° C., sodium borohydride (1.67 g, 0.044 mol) was added in 4 portions maintaining the temperature between −50° C. and −55° C. The resulting mixture was stirred for 1 h at the same temperature. After warming the reaction mixture to RT, it was concentrated to a residue under vacuum at about 45° C. Methanol (60 mL) was added and the resulting mixture was concentrated. The resulting residue was cooled to RT, water (50 mL) was added and the resulting aqueous mixture was extracted with ethyl acetate (100 mL×2). The combined organic layer was washed with saturated ammonium chloride solution (2×50 mL), water (50 mL) and brine solution (50 mL), and concentrated to obtain the title compound. Yield: 7.5 g.

EXAMPLE 4

Preparation of (3R,5S)-6-(tert-butyl-diphenyl-silanyloxy)-3,5-dihydroxy-hexanoic acid tert-butyl ester A solution of (5S)-6-(tert-butyl-diphenyl-silanyloxy)-5-hydroxy-3-oxo-hexanoic acid tert-butyl ester (20 g, 0.044 mol) in THF (60 mL) was stirred under nitrogen and methanol (20 mL) was added. The reaction mixture was stirred for 15 min. and cooled to −50° C. to −55° C. Anhydrous $CeCl_3$ (10.8 g, 0.044 mol) was added and stirred for 30 min., maintaining the temperature between −50 and −55° C. Sodium borohydride (2.5 g, 0.066 mol) was added in 6 portions maintaining the temperature between −70 and −90° C. The resulting mixture was stirred for 6 h at the same temperature. After warming the reaction mixture to RT, it was concentrated to a residue under vacuum at about 45° C. Methanol (60 mL) was added and the resulting mixture was concentrated. The resulting residue was cooled to RT, water (50 mL) was added and the resulting aqueous mixture was extracted with ethyl acetate (100 mL×2). The combined organic layer was washed with brine solution (50 mL), and concentrated to obtain the title compound. Yield: 17 g.

EXAMPLE 5

Preparation of (3R,5S)-3,5-dihydroxy-6-trityloxy-hexanoic acid tert-butyl ester A solution of (5S)-5-dihydroxy-3-oxo-6-trityloxy-hexanoic acid tert-butyl ester (20 g, 0.044 mol) in THF (75 mL) was stirred under nitrogen and methanol (20 mL) was added. Ti(IV)isopropoxide (12.5 g, 0.044 mol) was added and stirred for 30 min. at room temperature. After cooling the reaction mixture to −50° C. to −55° C., sodium borohydride (1.67 g, 0.044 mol) was added in 4 portions maintaining the temperature between −50° C. and −55° C. and stirred for 5 h at the same temperature. After warming the reaction mixture to RT, it was concentrated to a residue under vacuum at about 45° C. Methanol (60 mL) was added and the resulting mixture was concentrated. The resulting residue was cooled to RT, water (50 mL) was added and the resulting aqueous mixture was extracted with ethyl acetate (100 mL×2). The combined organic layer was washed with saturated ammonium chloride solution (2×50 mL), water (50 mL) and brine solution (50 mL), and concentrated to obtain the title compound. Yield: 14.5 g.

We claim:

1. A process for the preparation of a compound of Formula I

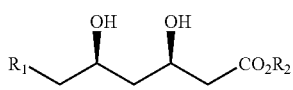

wherein $R_1$ is —CN, —OP, or alkyl, wherein P represents a tert-butyl-diphenyl-silanyl group or a triphenyl group; and $R_2$ is alkyl;

by reacting a compound of Formula II

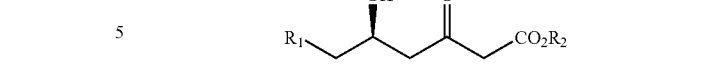

wherein $R_1$ is —CN, —OP, or alkyl, wherein P represents a tert-butyl-diphenyl-silanyl group or a triphenyl group; and $R_2$ is alkyl;

with sodium borohydride in presence of $CeCl_3$ or $Ti(OiPr)_4$.

2. The process of claim 1, wherein the $CeCl_3$ is anhydrous.

3. The process of claim 1, wherein the $CeCl_3$ is the heptahydrate.

4. The process of claim 1, wherein $R_2$ is t-butyl.

* * * * *